United States Patent [19]

Hoffman

[11] Patent Number: 4,870,015

[45] Date of Patent: Sep. 26, 1989

[54] METHOD AND COMPOSITION FOR PRODUCING LECTIN IN MICROORGANISMS

[75] Inventor: Leslie M. Hoffman, Madison, Wis.

[73] Assignee: Lubrizol Genetics, Inc., Wickliffe, Ohio

[21] Appl. No.: 844,406

[22] Filed: Mar. 26, 1986

Related U.S. Application Data

[63] Continuation of Ser. No. 446,438, Dec. 3, 1982, abandoned.

[51] Int. Cl.$^4$ .............. C12N 15/00; C12N 1/20; C12N 1/00; C12P 21/00; C12P 21/02; C07H 15/12

[52] U.S. Cl. .............. 435/172.3; 435/68; 435/70; 435/252.33; 435/320; 536/27; 935/9; 935/11

[58] Field of Search ............. 435/68, 172.3, 253, 435/320; 536/27; 935/9, 11

[56] References Cited

U.S. PATENT DOCUMENTS

| | | | |
|---|---|---|---|
| 4,293,652 | 10/1981 | Cohen | 435/172.3 |
| 4,356,270 | 10/1982 | Itakwa et al. | 435/172.3 |
| 4,357,421 | 11/1982 | Emtage et al. | 435/91 |

OTHER PUBLICATIONS

Hall et al., Genome Organization and Expression in Plants, Nato Adv. Study Inst. Series A, Life Sciences, vol. 29, pp. 259–272 (1979).
Poole et al., J. Mol. Biol., vol. 153, 273–289, Dec. 5, 1981.
Roberts et al., Methods in Enzymology, vol. 68, pp. 473–482, (1979).
Foriers et al., Physiol Vég. 17 (3), 597–606, (1979).
Goeddel et al., Nucleic Acids Res., vol. 8, pp. 4057–4074, (1980).
Suggs et al., PNAS USA, vol. 78, pp. 6613–6617. Nov. 1981.
Grunstein et al., PNAS USA, vol. 72, pp. 3961–3965, Oct. 1975.
Drickamer, The J. of Biol. Chem., vol. 256, pp. 5827–5839, Jun. 10, 1981.

*Primary Examiner*—Alvin E. Tanenholtz
*Attorney, Agent, or Firm*—Greenlee and Associates

[57] ABSTRACT

Methods and compositions for the construction of a recombinant vector containing plant or animal lectin DNA sequences, such vector being capable of being replicated, transcribed and translated in single cell hosts. The gene coding for the plant or animal lectin may be inserted into an expression vector which enables efficient production of the lectin protein.

40 Claims, 1 Drawing Sheet

FIG. 1

```
                                                                              GGATGAATGCATGATC

1  Met Ala Ser Ser Lys Leu Leu Ser Leu Ala Leu Phe Leu Ala Leu Leu Ser His Ala Asn      60
     ATG GCT TCC TCC AAG TTA CTC TCC CTA GCC CTC TTC CTT GCG CTT CTC AGC CAC GCA AAC

21  Ser Ala Thr Glu Ser Phe Ile Ile Asp Ala Phe Asn Lys Thr Asn Leu Ile Leu Gln         120
     TCA GCC ACC GAA ACC TCC ATC GAT GCG TTC AAC AAA ACC AAC CTT CTT CAA

41  Gly Asp Ala Thr Val Ser Asn Gly Asn Leu Gln Leu Ser Tyr Asn Ser Tyr Asp Ser         180
     GGC GAT GCC ACC GTC TCA TCC AAC GGC AAC TTA CAA CTA TCC TAT AAT TCA GAC TCT

61  Met Ser Arg Ala Phe Tyr Ser Ala Pro Ile Gln Ile Arg Asp Ser Thr Thr Gly Asn Val     240
     ATG AGC AGA GCC TTC TAC TCC GCC CCC ATC CAA ATC AGG GAC AGC ACC ACC GGC AAC GTC

81  Gly Ser Phe Asp Thr Asn Phe Thr Met Asn Phe Thr Arg Thr His Arg Gln Ala Asn Ser Ala 300
     GGC AGC TTC GAC ACC AAC TTC ACA ATG AAT TTC ACT CGC CAC CGC CAA GCA AAT TCC GCC

101  Val Gly Leu Asp Phe Val Leu Val Pro Gln Pro Glu Ser Lys Gly Asp Thr Val Thr         360
     GTT GGC CTT GAC TTT GTT CTC GTC CAG CCC GAA TCC AAA GGC GAT ACT GTG ACT

121  Val Glu Phe Asp Thr Phe Leu Ser Arg Ile Ser Ile Asp Gly Val Asn Asn Asp Ile Lys     420
     GTG GAG TTC GAC ACC TTC CTC AGC CGT ATT AGC GAC GGA GTT AAC AAC GAT ATC AAA

141  Ser Val Pro Trp Asp Val His Asp Tyr Asp Gly Ile Gln Asn Ala Glu Val Arg Ile Thr Tyr 480
     AGC GTG CCT TGG GAT GTA CAC GAC TAC GAC GGA CAA AAC GCC GAG GTT CGG ATC ACC TAT

161  Asn Ser Thr Lys Val Phe Ser Val Ser Leu Ser Asn Pro Ser Thr Gly Lys Ser Asn         540
     AAC TCC ACG AAG GTC TTC TCG TCA AAC CCT TCA ACG GGA AAG AGC AAC

181  Asn Val Ser Thr Thr Val Glu Leu Glu Lys Glu Leu Tyr Asp Trp Val Ser Val Gly Phe     600
     AAC GTC TCT ACA GTG GAG CTG AAA GAA GTT TAC GAC TGG GTG AGC GTT GGG TTC

201  Ser Ala Thr Ser Gly Ala Tyr Gln Trp Ser Tyr Glu Thr His Asp Val Leu Ser Trp Ser     660
     TCT GCC ACC TCA GGG GCT TAT CAA TGG AGC TAT GAA ACG CAC GAC GTC CTC TCT TGG TCT

221  Phe Ser Ser Lys Phe Ile Asn Leu Lys Lys Gln Lys Ser Glu Arg Ser Asn Ile Val Leu     720
     TTT TCT AAG TTC ATC AAT CTT AAG AAG CAA AAA TCT GAA CGT TCC AAC ATC GTC CTC

241  Asn Lys Ile Leu ***
     AAC AAG ATC CTC TAG ACTCCAAAAACCACCTTCACTGTGACAGTCTCATTCTTCTTTTTCCTGCTAATAATGTT
     CATCTGTCACACAAACTAAAATAAAATAAAATGGAAGCTCATATATATTTACACAAAAAAA...
```

METHOD AND COMPOSITION FOR PRODUCING LECTIN IN MICROORGANISMS

This is a continuation of application Ser. No. 446,438, filed Dec. 3, 1982 and now abandoned.

TABLE OF CONTENTS

1. Field of the Invention
2. Background of the Invention
   - 2.1. Lectin
   - 2.2. Recombinant DNA Technology
3. Summary of the Invention
4. Detailed Description of the Invention
   - 4.1. Extraction of Poly(A) RNA from Cotyledons
   - 4.2. Double-stranded cDNA Synthesis
   - 4.3. Isolation of Double-stranded Lectin cDNA
   - 4.4. Insertion of cDNA into a Cloning Vector
   - 4.5. Selection of Transformants Carrying Lectin cDNA Sequences
   - 4.6. Insertion of the Lectin Gene into an Expression Vector
   - 4.7. Isolation of Lectin Protein
5. Examples
   - 5.1. Total RNA Extraction
   - 5.2. Poly(A) RNA Isolation by Oligo(dT)-Cellulose Chromatography
   - 5.3. Reverse Transcription to Obtain Single-stranded Lectin cDNA
   - 5.4. Second Strand Synthesis and Tailing Procedures
   - 5.5. Size Selection of Lectin cDNA By Gel Electrophoresis
   - 5.6. Insertion of cDNA into a Plasmid
   - 5.7. Selection of Cells Transformed With Lectin cDNA Bearing Plasmid
   - 5.8. Production of Lectin Specific cDNA Probe

1. FIELD OF THE INVENTION

The present invention relates to the construction of recombinant vectors bearing the cDNA sequences for plant or animal lectins such as lectins of the plant family Leguminosae and the subfamily Papilonoideae, as well as the tribe Phaseoleae, the subtribe Phaseolinae, and, in particular, *Phaseolus vulgaris* cv. Tendergreen lectin, and to processes and compositions for making and using novel RNA and DNA sequences, vectors and microorganisms (both procaryotic and eucaryotic) to produce said recombinant vectors and lectin proteins.

The invention involves the extraction from cells of polyadenylated RNA [poly(A) RNA], the synthesis of double-stranded cDNA molecules from said RNA, and the insertion of the lectin cDNA sequence into a vector to form a recombinant cloning vector. This vector, once properly introduced into a bacterial cell, is capable of replicating and directing efficient expression of the cDNA in the form of lectin protein within the cell.

2. BACKGROUND OF THE INVENTION

2.1 LECTIN

Lectins are oligomeric sugar-binding proteins found in plant and animal cells as well as microorganisms and viruses. Although most lectins are glycoproteins, several lectins such as Concanavalin A, peanut lectin, and wheat germ agglutinin lack covalently bound carbohydrates and it is believed that the bound sugars do not play a significant role in the binding activity of lectin glygcoproteins.

At present, the biological role of lectin protein in nature is unclear. However, these proteins have been used extensively in biological research and medical diagnostics. The utility of lectins derives from their ability to bind reversibly to specific carbohydrate moieties without altering them chemically. Since each lectin binds specifically to a particular carbohydrate structure (e.g., *Phaseolus vulgaris* lectin binds to N-acetylgalactosamine linked to mannose), lectins provide a highly specific method for distinguishing and isolating oligosaccharides, glycoproteins and cells carrying these carbohydrate structures on their surfaces. Thus, lectins have been used to precipitate polysaccharides and glycoproteins, to agglutinate cells such as erythrocytes of specific blood groups (i.e., in blood typing) and to separate cancerous cells from normal cells. In addition, lectin affinity chromatography (in which lectin is covalently bound to a column matrix such as agarose) allows the separation and purification of soluble glycoproteins, glycopeptides, polysaccharides and glycosylated nucleic acids.

Another property of some lectins is their ability to act as mitogens, inducing mitosis in cultured cells. This effect is due in part to the protein's binding to the cell surface, although other cell surface interactions are believed to be involved as well.

Lastly, lectins are more toxic to cancerous cells in culture than to normal culture cell lines and have been used in the design and construction of new selective toxins.

Although plant lectins have been the most widely studied [see Lis and Sharon, Annu. Rev. Biochem. 42: 541 (1973)], lectins have been isolated from various animal sources including snails [see Cohen, et al., Life Sci. 4: 2009 (1965)], fish [see Pardoe and Uhlenbruck, J. Med. Lab. Technol. 27: 249 (1970)]and rabbits [see Lurrey and Ashwell, Proc. Natl. Acad. Sci., U.S.A. 73: 341 (1976)]. For example, mammalian hepatic lectin found in rabbit liver is belived to remove certain plasma proteins from the blood and has been shown to act as a mitogen for lymphocytes. In addition, lectin protein has also been found in fungi [see Sage and Corrett, J. Biol. Chem. 244: 4713 (1969)].

Although lectins vary in their carbohydrate specificity, cell binding and agglutinating ability and subunit arrangement, there appears to be a significant degree of homology between the amino acid sequences, overall molecular weights, subunit molecular weights and subunit numbers of various lectins from leguminous plants [see Foriers, et al., Physiol. Veg. 17(3): 597 (1979)]. In addition, animal lectins possess a subunit molecular weight and amino acid composition similar to that of plant lectins [see Brown and Hunt, Int. Rev. Cytol. 52: 277 (1978); Sharon and Lis, Science 177(4053): 949 (1972)].

The conventional methods for purification of lectins involved standard procedures of protein fractionation including ethanol precipitation, salt-induced crystallization, ion exchange chromatography and gel filtration. However, lectin purification is particularly difficult using standard procedures. Many lectins are composed of several subunits and these often become dissociated during extraction. In addition, the subunits may reassociate to form various permutations of the protein. Another problem is the physiochemical similarity between the various lectins making purification of a specific lectin difficult.

Increasingly, affinity chromatography has been utilized to isolate and purify lectins. A protein extract is passed over a column packed with an inert matrix to which a specific carbohydrate structure has been attached. The lectin specific for that carbohydrate structure binds to the moiety and is retained on the column while the rest of the protein extract is eluted off the column with buffer. To remove the lectin from the column, sugar solutions that inhibit lectin binding are utilized as eluents.

2.2 RECOMBINANT DNA TECHNOLOGY

Recombinant DNA techniques involve the insertion of specific DNA sequences into a DNA vehicle (vector) to form a recombinant DNA molecule capable of transforming host cells. Once introduced into these single cell hosts, the DNA sequences can be expressed in the form of a desired protein. The inserted DNA sequences are usually foreign to the vector, i.e., the insert and vector DNAs originate from organisms that do not exchange genetic information in nature. The inserted DNA may be eucaryotic or procaryotic in origin or may be wholly or partially synthesized.

Once constructed, the recombinant DNA molecule is usually introduced into a compatible host cell by the process of transformation. Selection of transformed cells is aided by the presence on the recombinant DNA molecule of a marker function such as antibiotic resistance. The host cell provides the transcriptional and translational machinery necessary for the expression of the inserted DNA within the cell, usually in the form of a protein. In addition, replication of the recombinant DNA within the host results in the production of multiple copies of the cloned DNA sequences. In order for the inserted sequences to be thus replicated and expressed, however, the appropriate replication, transcriptional and translational controls must be properly arranged on the recombinant DNA molecule.

U.S. Pat. No. 4,237,224 discloses the construction of a recombinant plasmid involving the use of restriction enzymes and the ligation of the inserted DNA and the plasmid DNA. The recombinant plasmid is then introduced into a host cell by transformation. U.S. Pat. No. 4,304,863 discloses another method of introducing recombinant plasmids into host cells involving a packaging/transduction system using bacteriophage vectors. Because of the general applicability of the methods described in these patents, U.S. Pat. Nos. 4,237,224 and 4,304,863 are incorporated by reference into the present application.

Several proteins have already been produced using recombinant DNA technology. These include somatostatin [Itakura, et al., Science 198: 1056 (1977)], the and β chains of human insulin [Goeddel, et al., Proc. Natl. Acad. Sci., USA 76: 106 (1979)], and human growth hormone [Goeddel, et al., Nature 281: 544 (1979)].

Generally, recombinant DNA techniques require that both the inserted sequences and the vector be linear double-stranded DNA molecules. In cloning or inserting eucaryotic genes into vectors which replicate in procaryotes, however, mRNA is usually utilized as the initial source of the inserted gene. The isolated mRNA transcript of the gene is reverse transcribed into a cDNA molecule which is then inserted into the vector. Isolation of mRNA as the gene source is much preferred to the direct insertion of eucaryotic genes into vectors since eucaryotic genes frequently contain intervening sequences (or introns) within the gene that do not code for any part of the gene product. These introns are not found in the mature mRNA since they are spliced or excised out of the precursor mRNA transcribed from the DNA. Thus, use of the mature mRNA transcript of a gene as the template for a cDNA molecule results in the production of a double-stranded DNA molecule coding for the gene product but lacking the non-coding intervening sequences found on the original genome.

RNA extraction from cells is typically carried out by removal of protein from the cell extract and precipitation of nucleic acid. A commonly used technique for isolating mRNA from such a RNA extract is oligo(dT)-cellulose chromatography. The mRNAs which contain polyadenylated sequences at their 3' ends are retained on the oligo(dT)-cellulose column [See Aviv and Leder, Proc. Natl. Acad. Sci., USA 69 (6): 1408 (1972)]. Hall, et al. [Proc. Natl. Acad. Sci., USA 75 (7): 3196 (1978)] have reported isolation of mRNA for Gl protein of French bean seeds of *Phaseolus vulgaris* using this method.

Once isolated, the mRNA is utilized as a template for reverse transcriptase, RNA-dependent DNA polymerase, to produce cDNA. In the typical reverse transcription reaction, a single-stranded cDNA is transcribed off of the mRNA. A hairpin structure at the 3' end of the first cDNA strand serves as a primer for synthesis of the second cDNA strand. Thus, a double-stranded cDNA molecule is produced but with a single-stranded loop at one terminus. This loop must be cleaved in order to obtain a double-stranded cDNA molecule suitable for cloning. Standard procedures utilize S1 nuclease to digest the loop. This digestion, however, may result in the loss of part of the cDNA corresponding to the 5' end of the mRNA (i.e., the 3' end of the cDNA). Therefore, full length cDNA of a structural gene is frequently not obtained.

Several procedures have been reported for the construction of full length cDNA without the need for S1 nuclease digestion. According to Land, et al. [Nucleic Acid Res. 9: 2251 (1981)], poly(A) RNA is reverse transcribed in the presence of actinomycin D to form an RNA/cDNA hybrid which is extracted and treated with alkali to produce single-stranded cDNA. This cDNA is then (dC)-tailed at its 3' terminus, an oligo-(dG)-homopolymer is allowed to anneal to the (dC)-tail and the second cDNA strand is then transcribed using the (dG)-homopolymer as a primer. This method prevents the hairpin loop formation and results in the production of a full length double-stranded cDNA molecule.

Furthermore, actinomycin D is believed to aid in the production of full length cDNA. A Ribonuclease H activity is intrinsically associated with the reverse transciptase enzyme. This activity degrades the RNA template into oligo-ribonucleotides that can anneal to the cDNA strand as it is being transcribed and prime the synthesis of short second strand cDNA fragments which anneal to the first cDNA strand. The hydrolysis with alkali degrades all RNA in the reaction mixture including the oligo-ribonucleotide primers and denatures all DNA, resulting in a mixture of full length cDNA as well as smaller anti-complementary DNA fragments (from the RNA priming). These fragments will subsequently be tailed, primed and cloned as per this procedure and thus decrease the yield of full length cDNA clones. By blocking the DNA templated DNA polymerase activity of reverse transcriptase, actinomycin D is thought to prevent this second or anti-complementary strand synthesis. However, actinomycin D is not an efficient inhibitor of the enzymatic activity. Thus, a significant amount of second strand synthesis occurs.

The recent method of Okayama and Berg [Mol. Cel. Biol. 2: 161 (1982)] involves the insertion of a poly(A) mRNA molecule into a plasmid that has been (dT)-tailed and acts as a primer for cDNA synthesis. The final product is an mRNA/cDNA hybrid molecule. The mRNA strand is then replaced with a corresponding DNA strand by the actions of RNase H, DNA polymerase I and DNA ligase to form a double-stranded cDNA insert within the plasmid.

Additionally, Kacian and Myers [Proc. Natl. Acad. Sci., U.S.A. 73: 2191 (1976)] have reported that sodium pyrophosphate and ribonucleoside triphosphates are effective at inhibiting smaller cDNA synthesis during the reverse transcription of mRNA to yield single-stranded cDNA.

3. SUMMARY OF THE INVENTION

Methods and compositions are provided for the construction of a recombinant vector bearing the cDNA sequence for lectin, a sugar-binding protein. Upon transformation of cells with this vector, the cDNA sequence can be expressed in the form of lectin protein.

The invention involves the extraction of polyadenylated RNA from cells. According to the preferred embodiment of the present invention, total RNA is extracted from plant seed cotyledons and poly(A) RNA is isolated from this extract by oligo(dT)-cellulose chromatography. Since most eucaryotic messenger RNAs (mRNAs) bear a polyadenylated nucleotide sequence at their 3' terminus, oligo(dT)-cellulose chromatrography provides a relatively easy method of isolating these messenger RNAs.

Although RNA may be extracted from plant leaves and roots, RNA extraction from seed cotyledons is preferred because only a few types of proteins are present at high concentration within these embryonic leaf-like structures. Thus, an extract of total RNA from cotyledons, especially during the 9 mm–14 mm stages of seed development, includes significant amounts of only a limited number of types of RNA transcripts or messengers (which code for these proteins), one of which is the transcript coding for lectin protein.

The poly(A) RNA is then reverse transcribed to form a single-stranded cDNA molecule annealed to the original RNA template. The RNA is then hydrolyzed and the cDNA strand is used as a template for the synthesis of a second or anti-complementary cDNA strand. This synthesis involves the attachment of a homopolymeric oligonucleotide tail (e.g., a poly(dC) or poly(dG) tail) to the 3' end of the first cDNA strand and the hybridization of a complementary homopolymeric oligonucleotide chain to this tail which acts as a primer in the synthesis of the complementary second strand (anti-complementary strand). This double-stranded cDNA is then tailed at its 3' termini with a deoxynucleotide homopolymer to facilitate subsequent insertion into a cloning or expression vector.

Reverse transcription of the total cell poly(A) RNA extract yields a cDNA population consisting of different cDNA molecules coding for a variety of proteins. However, the cDNA coding for lectin may be isolated based on its size as resolved by polyacrylamide or agarose gel electrophoresis according to techniques well known in the art. This size selection is optional, however, due to a subsequent screening technique for lectin cDNA transformants, but may be carried out either at this stage of the invention or before the double-stranded cDNA is tailed as an additional selection step.

Alternatively, the initial poly(A) RNA extract may be enriched for lectin mRNA before reverse transcription by sucrose gradient centrifugation. Lectin mRNA sediments in the gradient at 13S, can be easily collected, and reverse transcribed as described above to produce a lectin cDNA population.

The full length or nearly full length tailed double-stranded cDNA is next inserted into a DNA vector. This can be accomplished by tailing the 3' termini of the cleaved DNA vector to complement the homopolymeric tails on the cDNA. Alternatively, both the cDNA and vector DNA can be modified by litgating onto their termini linker nucleotide sequences that contain specific chemically synthesized restriction enzyme recognition sites. Thus, a desired restriction site is produced which, on cleavage with the appropriate enzyme, results in complementary termini. Additionally, the cDNA and vector DNA may be modified to produce blunt ends which can then be ligated together to produce a recombinant expression vector bearing a lectin cDNA insert.

The recircularized recombinant vector containing the lectin cDNA insert within its ampicillin resistance gene is then used to transform cells. Selection of ampicillin-sensitive cells and screening of lectin cDNA-containing colonies by colony hybridization techniques allows the improved isolation of cells transformed with the lectin cDNA-bearing recombinant vectors. These cells are capable of expressing the lectin sequences resulting in the production of lectin protein.

The present invention can be more fully understood by reference to the following detailed description and the appended FIG. 1 which represents the lectin cDNA sequence and the amino acid sequence predicted therefrom. DNA sequencing was performed using a modification of the procedure of Maxam and Gilbert [see Maxam and Gilbert, Proc. Natl. Acad. Sci., U.S.A. 74: 560 (1977) and Garoff and Ansorge, Anal. Biochem. 115: 450 (1981)].

4. DETAILED DESCRIPTION OF THE INVENTION

4.1. EXTRACTION OF POLY(A) RNA FROM COTYLEDONS

To extract RNA from plant seeds, cotyledons excised from seeds are subjected to freezing and thawing followed by mixture with an EGTA [ethylenebis(oxyethylenenitrilo)tetraacetic acid]-SDS (sodium dodecyl sulfate) solution and mechanical grinding using an homogenizer. This treatment breaks the cells, chelates calcium and other divalent cations, solubilizes the various cellular components and denatures proteins. The solution is then treated with Proteinase K, an enzyme that digests proteins and irreversibly inactivates enzymes, such as nucleases. These proteins can be discarded in the form of a pellet after precipitation of SDS-protein complexes by chilling, addition of potassium ions, and centrifugation. RNA is precipitated out of solution by treatment of the supernatant with lithium chloride which selectively precipitates large molecular weight single-stranded nucleic acids. Thus, cellular double-stranded DNA as well as low molecular weight RNAs remain in the supernatant and can be discarded.

The RNA is resolubilized with potassium acetate and reprecipitated with ethanol to remove lithium ions. This precipitate contains various types of RNAs, mostly messenger and ribosomal RNAs, found within cells.

In order to isolate poly(A) RNA, oligo(dT)-cellulose chromatography is utilized. The extracted RNA is dissolved in an application buffer solution (such as TRIS-HCl/NaCl) and applied to an oligo(dT)-cellulose column previously washed with the buffer. Oligo(dT)-cellulose is an affinity matrix consisting of chains of deoxythymidylate covalently linked to cellulose via the 5' phosphate of the oligonucleotide. The polyadenylated sequences on the RNA molecules anneal via hydrogen bonds to the complementary oligo(dT) sequences on the column and the RNA is retained. Nonadsorbed material is eluted by continuous washing with application buffer. Removal of the poly(A) RNA from the column is accomplished by elution with a low salt buffer. Poly(A) RNA may also be eluted with water. The RNA is then precipitated from the elution buffer with potassium acetate and ethanol. For efficient removal of contaminating RNAs, the extracted RNA is subjected to two cycles of oligo(dT)-cellulose chromatography.

It should be noted that while cells may contain various types of polyadenylated RNAs, a large proportion of any poly(A) RNA extract will consist of messenger RNAs, the RNA transcripts of genes which provide the information necessary for the translation of the proteins for which the genes code.

4.2. DOUBLE-STANDARD cDNA SYNTHESIS

The next phase of the invention involves the reverse transcription of the above-isolated poly(A) RNA to yield full length or nearly full length double-stranded cDNA.

The poly(A) RNA is transcribed in vitro using reverse transcriptase or RNA-dependent DNA polymerase, an enzyme that utilizes RNA as a template for the synthesis of a complementary strand of DNA. The presence of a primer (of DNA or RNA) which anneals to the 3' end of the RNA template is necessary for the transcription; the enzyme elongates the primer in the 5' to 3' direction by sequential addition of deoxynucleoside monophosphates according to the base pattern dictated by the RNA template. Where the template used is poly(A) RNA, an obvious primer is oligo(dT), a deoxythymidylate chain which anneals to the polyadenylated sequences at the 3' end of the RNA. Thus, the in vitro reverse transcription system includes the poly(A) RNA template, the reverse transcriptase enzyme, the oligo(dT) primer and each of the four deoxynucleoside monophosphates for addition onto the primer to produce a cDNA strand complementary to the RNA. One of the deoxynucleotides is $^{32}P$ radio-labeled to allow detection of the cDNAs incorporating it in subsequent phases of the invention.

The method of the present invention essentially follows the procedure of Land, et al. (see Section 2.2).

After 45 minutes, the reverse transcription reaction is stopped and the full length cDNA/mRNA hybrid produced is extracted from the mixture with chloroform isoamyl alcohol or phenol to remove proteins, and then hydrolyzed with alkali to degrade the RNA template. Largely full length single-stranded cDNA is then isolated by gel filtration and precipitation with ethanol.

Double-stranded cDNA is then synthesized from the cDNA strand in the following manner. The single-stranded cDNA is tailed at its 3' terminus with a homopolymeric oligonucleotide (e.g., poly (dC) by the action of a terminal deoxyribonucleotidyl transferase, an enzyme that adds, in the presence of the appropriate deoxynucleotide triphosphate, a single-stranded homopolymer of the deoxynucleotide to the cDNA 3' terminus. The tailed cDNA is extracted and isolated by column chromatography followed by ethanol precipitation.

Next, a homopolymeric oligonucleotide, which is complementary to the 3' tail of the cDNA molecule prepared above (e.g., a poly(dG) homopolymer), is hybridized to the 3' homopolymeric tail to serve as a primer for the transcription by reverse transcriptase of the second cDNA strand. In this transcription, the first cDNA strand is now the template for the synthesis of a second strand (the anti-complementary strand); the two strands anneal together due to hydrogen bonding between their complementary bases. The cDNA is purified by gel permeation chromatography an dthen tailed under the same conditions as described above to produce a double-stranded DNA molecule with homopolymeric single-stranded tails or extensions (at least approximately 10 bases long) at the 3' end of each strand (e.g., the cDNA may be tailed with poly(dC)).

4.3. ISOLATION OF DOUBLE-STRANDED LECTIN cDNA

Since the reverse transcription reactions described above are performed on total cell poly(A) RNA consisting of the mRNA transcripts of various genes, a variety of double-stranded cDNA molecules coding for various proteins, including lectin, will be produced.

Lectin cDNA can be size selected, however, by polyacrylamide or agarose gel electrophoresis. This technique involves the migration of charged molecules through a porous gel due to an electric field set up in a buffer permeating the gel. The electrophoretic mobility of nucleic acids is related to their molecular weights and so application of a cDNA population onto the gel allows separation of the molecules according to size.

According to the method of this invention, the tailed double-stranded cDNAs are applied to an acrylamide gel having an acrylamide concentration between 5 and 7.5%. Glycerol may be added to the gel to improve separation of the migrating bands of molecules. The various radio-labeled cDNAs in the sample form bands at different levels along the vertical gel and can be detected by autoradiography, a procedure involving the exposure of film to the radioactive gel to form a picture of the banding of the molecules on the gel, much like a film negative [for review of these methods, see Southern, Methods in Enzymology 68: 152 (1980)].

Based on the calculated molecular weight of lectin cDNA and the migration of marker molecules of known molecular weights, the band representing lectin cDNA molecules can be identified and cut out of the gel. This gel portion is then crushed and allowed to incubate in a high salt buffer overnight. The cDNA diffuses out of the gel and into the buffer. To further purify the lectin cDNA from any contaminating acrylamide, the buffer is centrifuged through a narrow tube filled with glass wool. The acrylamide is caught on the wool and the double-stranded lectin cDNA can be decanted for further use.

4.4. INSERTION OF cDNA INTO A CLONING VECTOR

The tailed lectin cDNA is then inserted into a cloning vector that has been cleaved at a unique restriction site and tailed with a homopolymer that is complementary to the 3' tails of the cDNA molecule. For example, when the cDNA is poly(dC)-tailed, the circular plasmid pBR322 is cut with the restriction enzyme Pst I at the sequence CTGCAG (a unique site on the plasmid) and dGMP-tailed as describeed above. At least approximately 10 dGMP nucleotides are added to each 3' end of the double-stranded plasmid DNA (now a linear molecule via the cleavage by Pst I).

The previously prepared (dC)-tailed lectin cDNA is allowed to anneal to the Pst I cleaved, (dG)-tailed plasmid DNA to form a recircularized recombinant plasmid containing the lectin cDNA insert. Ligation of the cDNA with the plasmid DNA is optional.

4.5. SELECTION OF TRANSFORMANTS CARRYING LECTIN cDNA SEQUENCES

The resultant recombinant vector is then used to transform cells by techniques well known in the art. Transformed cells are selected based upon the expression of gene markers present on the vector such as antibiotic resistance. Expression of such markers indicates that the vector is replicating. Since Pst I cuts pBR322 within its ampicillin resistance gene, cells transformed with a recombinant plasmid bearing the lectin cDNA insert in the proper position will be ampicillin-sensitive and tetracycline-resistant (the tetracycline resistance gene also borne on the plasmid is unaffected by the cDNA insertion). Cells subjected to the transformation process are therefore grown in the presence of tetracycline such that only cells transformed with functioning plasmids will form colonies (as opposed to nontransformed cells). Upon addition of ampicillin to replicate plates, ampicillin-sensitive colonies, i.e., those cells bearing the proper cDNA insert within the ampicillin resistance gene, stop growing. These colonies can then be picked from the original plates and grown up in culture. Thus, cells transformed with a plasmid bearing the cDNA insert within the ampicilin resistance gene are selected.

While the gel electrophoresis procedure detailed earlier provides a cDNA population size selected for lectin sequences, there may still be amounts of other similarly sized cDNAs coding for other proteins contaminating the population. To further screen for cells carrying the lectin cDNA as opposed to these other cDNAs, colony hybridization techniques are utilized.

The ampicillin-sensitive colonies are grown on different areas of a nitrocellulose filter. The cells are lysed and the cellular DNAs are denatured and fixed onto the filters. To this colony DNA "print," a radioactive ("labeled") 13S cDNA population enriched for lectin sequences can be hybridized. This labeled cDNA may be obtained by reverse transcription in the presence of radioactive deoxynucleotides of lectin mRNA isolated by sucrose gradient centrifugation of a cotyledon poly(A) RNA extract; the lectin mRNA sediments at 13S. The labeled cDNA will only anneal to the colony DNA bearing lectin sequences. The site of hybridization (i.e., the appropriate colonies) can be determined by autoradiography, which detects the labeled cDNA probe on X-ray film. Those colonies can then be grown up in culture.

A further screening procedure involves the subsequent hybridization of these detected lectin cDNA-bearing colonies via the same hybridization procedure but now with a radio-labeled phaseolin cDNA clone. The colonies to which this probe hybridizes contain 16S sequences that encode phaseolin (a major storage protein of Phasolus) which may not have been completely removed by the earlier gel electrophoresis procedure, and can be eliminated. This double screening procedure results in improved isolation of clones containing recombinant plasmids bearing lectin cDNA sequences. One such recombinant plasmid containing a lectin cDNA insert is pPVL 134. The DNA insert (encoding lectin) can be further characterized by restriction mapping the cloned DNA by gel electrophoresis, and by hybridization of radiolabelled lectin cDNA to the gel pattern transferred to nitrocellulose [Southern, Methods in Enzymology, 68: 152 (1980)].

4.6. INSERTION OF THE LECTIN GENE INTO AN EXPRESSION VECTOR

Expression vectors are cloning vectors which contain certain transcriptional and translational controls in order to properly direct host cell expression of the inserted DNA sequences [see Roberts and Lauer, Methods in Enzymology 68: 473 (1979); U.S. Pat. No. 4,332,892]. First, a promoter sequence to which RNA polymerase binds and initiates transcription of DNA sequences should be present on the vector. Strong promoters, i.e., those with increased ability to promote transcription, are preferred in order to obtain high levels of gene expression. Examples of promoters that may be utilized in expression vectors in the *E. coli* host cell system include any promoters isolated from *E. coli* such the lac or rec A promoters as well as promoters on its bacteriophages or its plasmids, $P_R$ and $P_L$ promoters of coliphase lambda and promoters chemically synthesized or produced by recombinant DNA techniques. Secondly, translational controls in the form of specific initiation signals should be incorporated into the vector. Efficient translation of mRNA in procaryotic host cells requires the presence of the Shine Dalgarno (SD) sequence located before the AUG start codon of the mRNA. It is believed that this sequence acts as a ribosome binding site allowing correct positioning of the ribosome in the initiation of protein translation. Thus, the DNA sequence corresponding to this SD-AUG signal should be present on the vector DNA in order for mRNA transcribed off of the vector to contain the appropriate translational control. SD-ATG DNA sequences utilized in this way include sequences from the cro or N genes of coliphage lambda, the *E. coli* lac and tryptophan genes, and any sequences chemically synthesized or produced by recombinant DNA techniques.

Insertion of the transcriptional and translational control sequences into the vector may be accomplished by any of the methods previously described for insertion of the lectin cDNA or by any other technique known in the art. Once these controls are in place on the vector, the lectin sequences can be inserted at a specific site relative to the controls such that the lectin gene is in the correct reading frame for proper expression of the gene.

4.7. ISOLATION OF LECTIN PROTEIN

The selected cells expressing the lectin cDNA sequences may be cultured in a large volume and the lectin protein isolated by standard techniques of protein purification. Lectin may be secreted into the periplasmic space or to the inner membrane of *E. coli*.

5. EXAMPLES

The following examples demonstrate the methods of the invention utilizing *P. vulgaris* cv. Tendergreen lectin RNA as a template for the synthesis of double-stranded lectin cDNA. The cloning vector used for transformation of *E. coli* HB101 cells was plasmid pBR322.

5.1. TOTAL RNA EXTRACTION

Mid-maturation stage bean cotyledons were quick-frozen in liquid nitrogen after removal of the seed coat and embryonic axis and conveniently stored at about −70° C. for later use. To isolate total RNA, 50 g of frozen cotyledons were warmed to −20° C. and 0.1 g of solid dithiothreitol (DDT, which is used at a concentration of 5mM in the final buffer) was added. 130 ml of a buffer that had been adjusted to pH 9.0 with sodium hydroxide and which contained 0.2M sodium borate, 1% SDS, and 30mM EGTA, was heated to 100° C. and added to the cotyledons which were then disrupted in a Polytron homogenizer (Brinkman Instruments, Westbury, N.Y.). Isoamyl alcohol was added as needed to reduce foaming. After cooling below 40°–45° C., 65 mg of Proteinase K (0.5 mg/ml buffer) was added and the mixture was incubated 1 hour at 37°–40° C. After addition of 10 ml of 2.0M potassium chloride, the mixture was cooled on ice and the resulting precipitate was removed by centrifugation for 10 minutes at 12,000xg. Solid lithium chloride was added to the supernatant to the concentration of 2M and after standing overnight at 4° C., the resulting precipitate was collected by centrifugation for 10 minutes at 12,000xg and washed twice with cold 2M lithium chloride. The lithium precipitate was dissolved in 2% (wt./vol.) potassium acetate, pH 5.5, and insoluble material was removed by centrifugation for 10 minutes at 12,000xg. Addition of 2.5 volumes of ethanol and incubation overnight at −20° C. resulted in reprecipitation of RNA which was collected by centrifugation for 10 minutes at 12,000xg.

5.2. POLY(A) RNA ISOLATION BY OLIGO(dT)-CELLULOSE CHROMATOGRAPHY

The ethanol precipitate from the total RNA extraction was dissolved in 10mM tris(hydroxymethyl) aminomethane (Tris) acetate, pH 7.5 (low salt buffer). The RNA solution was heated in a boiling water bath for one minute and quench-cooled in an ice water bath for two minutes to disaggregate the RNA. After addition of sodium chloride to a concentration of 0.4M, the solution was applied to an oligo(dT)-cellulose column which was then washed with 0.4M sodium chloride, 10mM Tris acetate, pH 7.5 (high salt buffer) until an ultraviolet column monitor set at 254 nm showed that unbound RNA had been removed. Bound poly(A) RNA was then eluted with low salt buffer, and the column was then washed with high salt buffer preparatory to further use of the column. As the unbound RNA still contained poly(A) RNA due to the limited capacity of the oligo(dT) column, this procedure was repeated several times until no further poly(A) RNA binding was observed by the column monitor during elution with low salt buffer. The poly(A) RNA fractions were then pooled and subjected to heating and quench-cooling as above. After addition of solid sodium chloride to 0.4M, the poly(A) RNA was subjected to a second cycle of oligo(dT)-cellulose chromatography as above. The materials eluted from the two procedures were pooled, a final concentration of 2% (wt./vol.) potassium acetate, pH 5.5, were added and 2.5 volumes of ethanol was added to precipitate the RNA overnight. The poly(A) RNA precipitate was collected by centrifugation for 10 minutes at 12,000xg, dissolved in a small volume (0.5 ml) of sterile distilled water, and stored at −70° C.

5.3. REVERSE TRANSCRIPTION TO OBTAIN SINGLE-STRANDED LECTIN cDNA

Poly(A) RNA enriched for 13S and 16S RNA by sucrose gradients centrifugation was reverse transcribed in 0.25 ml of a mixture containing 50mM Tris hydrochloride (Tris-HCl), pH 8.3, 6mM magnesium chloride, 2mM DTT, 50mM potassium chloride, 5 µg/ml oligo (dT) primer, 400 units/ml human placental ribonuclease inhibitor, 80 µg/ml poly(A) RNA, 250 units/ml of reverse transcriptase, 100 µM $\alpha[^{32}P]$-deoxycytosine triphosphate (dCTP, 0.97 Ci/mmole), and 500 µM each of deoxyadenosine triphosphate (dATP), deoxyguanosine triphosphate (dGTP), and deoxythymidine triphosphate (dTTP). After incubation at 42° C. for 45 minutes, the reaction was stopped by addition of 0.02 ml of 0.25M ethylenediaminetetraacetic acid (EDTA) that had been neutralized with sodium hydroxide. The mixture was extracted once with 0.25 ml of chloroform:isoamyl alcohol (24:1, vol.:vol.) and the organic phases were re-extracted with 0.1mM Tris-HCl, pH 7.5, 1mM EDTA. The aqueous phases were pooled and RNA was hydrolyzed by the addition of 0.02 ml of 6M sodium hydroxide and incubation overnight at 25° C. Free nucleotides were removed after neutralization with 0.02 ml of 6M hydrochloric acid and 0.004 ml of 2M Tris-HCl by chromatography on a small column of Sephadex G-75 (medium) and the fractions containing the labeled single stranded cDNA were identified in a scintillation counter. To the pooled fractions, having a volume of about 1.5 ml, were added 0.15 ml 3M sodium acetate and about 3 ml of ethanol. After standing at −20° C. for 24 hours or longer a precipitate which contained about 3 µg of cDNA was collected by centrifugation at 12,000xg for 10 minutes.

5.4. SECOND STRAND SYNTHESIS AND TAILING PROCEDURES

An aliquot of single-stranded cDNA was tailed at its 3' terminus with cytosine residues in a reaction which contained cDNA, 0.1M potassium cacodylate buffer, pH 7.0, 10mM DTT, 0.1 mg/ml bovine serum albumin, 1mM cobalt chloride, 10.9 µM/ml $[^{3}H]$-deoxycytosine triphosphate (73 µCi/ml), and 517 units/ml terminal transferase. After 4 minutes at 37° C., the reaction was stopped by addition of 0.01 volumes of diethylpyrocarbonate. The reaction mixture was extracted with chloroform-isoamyl alcohol and the resulting organic phase was twice re-extracted with 10mM Tris-HCl, pH 7.5, 1mM EDTA. After the aqueous phases were pooled, the tailed cDNA was separated from unincorporated nucleotides by Sephadex G-75 column chromatography, and concentrated by ethanol precipitation. The cDNA was dissolved in 0.1 ml of 0.25M Tris-HCl, pH 8.3, 0.15M potassium chloride, 0.05M magnesium chloride, in the presence of 30 µg/ml of oligo(deoxyguanidylic acid)$_{12-18}$ primer. The mixture was annealed at 68° C., 54° C. and 42° C. for 5 minutes, 10 minutes, and 15 minutes, respectively, and was finally placed in an ice bath. The mixture was then added to a solution with final concentrations of 10mM DTT, 60

μM α-[32P]deoxycytosine triphosphate (about 0.5 mCi/ml), 1mM each of dGTP, dATP, and dTTP, and 250 units/ml reverse transcriptase. The second strand synthesis was allowed to proceed at 37° C. and 42° C. for 10 minutes and 50 minutes, respectively. The reaction was stopped by adjusting the solution to 0.4M sodium chloride, 0.2M EDTA, 0.1% (wt./vol.) SDS. Small molecules were removed by gel permeation chromatography (Sephadex G-75) after incubation overnight at 4° C. Approximately 0.128 μg of double-stranded cDNA was recovered.

The double-stranded cDNA was tailed with oligo(cytidylic acid) using conditions as described above. The reaction was terminated after 2 minutes at 37° C. by addition of 0.01 volume of 10% (vol./vol.) diethylpyrocarbonate. It was found that an average of about 65 cytidylic acid residues had been added to each end.

5.5. SIZE SELECTION OF LECTIN cDNA BY GEL ELECTROPHORESIS

Full length double-stranded lectin cDNA was purified by electrophoresis through a 3 mm thick gel, 6% (wt./vol.) acrylamide and 0.3% (wt./vol.) N,N'-methylene biascrylamide polymerized with 0.015% (wt./vol.) ammonium persulfate and 0.03% (wt./vol.) N,N,N',N'-tetramethylethylenediamine (TEMED) in a buffer consisting of 90mM Tris, 90mM boric acid, 3mM EDTA, and 25% glycerol. The DNA was applied to the gel in a sample buffer consisting of 90mM Tris, 90mM boric acid, pH 8.3, 3mM EDTA, 12% sucrose, 1% sarkosyl and 15mM sodium chloride, and allowed to run for 1.75 hour at about 100 volts and then 35 volts (about 15mA) overnight. The band containing the full length 13S cDNA, located by autoradiography and comparison to markers of known molecular weights, was cut out of the gel. The cDNA was eluted by crushing the piece of gel and incubating it overnight at 37° C. in 8 ml of solution consisting of 0.5M ammonium acetate, 0.01M magnesium acetate, 1mM EDTA, 0.1% (wt./vol.) SDS. Polyacrylamide fragments were removed by centrifuging the mixture through a siliconized glass wool plug, which was then washed with elution buffer. Eluted 13S cDNA was precipitated at −70° C. (dry ice-ethanol bath) for 10 minutes after addition of 3 volumes of ethanol, dissolved in a small volume of 0.3M sodium acetate, reciprocated at −70° C. with 3 volumes of ethanol, redissolved in a very small volume of water.

5.6. INSERTION OF cDNA INTO A PLASMID

The plasmid pBR322 (1 μg/50 μl) was cut with the restriction enzyme PstI (1 unit/1 μg DNA, New England Biolabs, Beverly, Mass.) for 1 hour in the presence of 50mM NH2SO4, 20mM Tris-HCl, pH 7.5, 10mM MgCl2 and 100 μg/ml BSA at 37° C., tailed with oligo(deoxyguanidylic acid) using conditions analogous to those described in Section 5.5 for the tailing of the cDNA insert, and frozen in aqueous solution for later use. About 25 ng of tailed, double-stranded cDNA and about 0.25 μg of tailed pBR322 were mixed in the presence of 0.1M sodium chloride, 10mM Tris-HCl, pH 7.5, and 1mM EDTA. The DNAs were annealed by heating the mixture in a beaker of water held at 65° C., then slowly cooled to 42° C., and incubated for approximately 2 hours in a 42° C. water bath. The mixture was then further cooled by transferring the entire bath to a 4° C. cold room for 16 hours.

5.7. SELECTION OF CELLS TRANSFORMED WITH LECTIN cDNA BEARING PLASMID

To obtain cells competent for transformation, a 50 ml overnight culture of *E. coli* HB101 bwas grown in a medium consisting of 10 g NZ-amine, 5 g yeast extract, 5 g sodium chloride, 100 mg DL-α, -diaminopimelic acid, 40 mg thymidine, and water to 1 liter (NZYdt). 0.5 ml of the overnight culture was added to 50 ml of fresh NZYdt and grown until it had an absorbence of 0.2 at 650 nm. Cells were then chilled on ice for 10 minutes, centrifuged for 10 minutes at 2,550xg max at a temperature of 4° C., and gently resuspended in 20 ml of cold 0.1M calcium chloride. After incubation on ice for 20 minutes, the cells were resedimented as above, and after very gentle resuspension in 0.5 ml of 0.1M calcium chloride, were left on ice in a 4° C. cold room overnight. The recombinant plasmid, which was in 0.02 ml of water, was added to 0.1 ml of competent cells, left on ice for 10 minutes and then at 37° C. for 5 minutes, and 4 ml of NZYdt was added. After growth for 1.5 hour on a rotating drum, tetracycline was added to the culture to a concentration of 25 μg/ml, cultured for 0.5 hour, and spread on plates containing NZYdt supplemented with 25 μg/ml tetracycline and solidified with 1.5% (wt./vol.) agarose. Two hundred eighty two tetracycline resistant colonies were recovered. One hundred thirty seven colonies were found to be carrying wild-type pBR322 and continued to grow when tested on plates additionally supplemented with 50 μg/ml ampicillin.

One hundred and forty five ampicillin-sensitive colonies were grown on nitrocellulose filters which had been previously placed on L plates (1% tryptone, 0.5% yeast extract, 0.05% sodium chloride, solidified in 1.5% agar) which contained 25 μg/ml tetracycline. After the colonies grew up, the filters were removed from the L plates and placed on top of Whatman 3 mm filter paper previously saturated with 0.5M sodium hydroxide and 1.5M sodium chloride which lyses the cells and denatures the cellular DNA. As a result, the DNA was fixed to the filter. After 5 minutes the nitrocellulose was transferred to a filter saturated with 1M Tris-CHl, pH 7.0, and 3M sodium chloride. After 10 minutes the filter was washed in a Buchner funnel with about 20 ml of a solution consisting of 0.15M sodium chloride, 0.03M Tris-HCl, pH 7.5, and 0.01M EDTA (STE). The filters were incubated for 45 minutes in petri dishes containing 8 to 10 ml of STE containing 50 μg/ml Proteinase K, and again washed with STE. Twice the filters were washed with 70% (vol./vol.) ethanol and dried for 5 to 10 minutes on the funnel. After air drying for an additional 10 to 15 minutes, the filters were placed in a 65° C. vacuum oven for over 2 hours. Preincubation of the nitrocellulose filters was carried out at 67° C. in a solution of 0.9M sodium chloride, 0.09M sodium citrate, pH 7.0 (6×SSC), 0.06% (wt./vol.) each of Ficoll, bovine serum albumin, and polyvinylpyrrolidone (3×Denhardt's solution) for 4 hr. Hybridization to a lectin specific probe was carried out for 21 hours under the same conditions used for the preincubation. The nitrocellulose filters were then washed at 67° C. for 45 minutes in 3×SSC, 0.5% SDS. The filters were exposed to film at −70° C. for approximately 18 hours in the presence of an intensifying screen. The procedure was repeated with a phaseolin (storage protein) specific probe in order to help eliminate false positives. Six clones were judged to be good candidates for lectin and several have been confirmed by sequencing.

5.8. PRODUCTION OF LECTIN SPECIFIC cDNA PROBE

The lectin specific probe was a cDNA that had been reverse transcribed from sucrose gradient purified 13S (lectin enriched) poly(A) RNA. Poly(A) RNAs were separated according to their respective sedimentation coefficients by centrifugation through "linear-log" sucrose gradients in a Beckman SW41Ti swinging bucket rotor. The gradients were prepared by pouring layers of sucrose solutions of the appropriate density. The sucrose solutions were buffered with 10mM Tris acetate, pH 7.5. The layers of sucrose concentrations (% wt./vol.) 32.5, 27, 21, 16, 10, and 0 had volumes of 1.8, 3.5, 2.3, 1.5, 1.3, and 1.2 ml, respectively. The gradient was centrifuged at 4° C. for 17 hours at 36,000 rpm (220,000xg max, 160,000xg ave) and was fractionated in an ISCO fractionator by injection of a 50% (wt./vol.) sucrose pad under the gradient after bottom puncture. The 13S enriched RNA fraction was made 2% (wt./vol.) in potassium acetate and 2.5 volumes of ethanol were added. After standing overnight at −20° C., a precipitate was collected by centrifugation for 15 minutes at 12,000xg and dissolved in sterile distilled water. The RNA was then reverse transcribed in the presence of 500 units/ml human placental ribonuclease inhibitor, 2mM DTT, 25mM Tris-HCl, pH 8.3, 25mM potassium chloride, 5 μg/ml oligo(deoxythymidylic acid), 6mM magnesium chloride, 5% (vol./vol.) glycerol, 26.5 μM α-[$^{32}$P] deoxycytosine triphosphate (1.2mCi/ml), and 0.5mM each of dATP, dTTP and dGTP. The oligo(dT) primer was annealed to the mRNA at 55° C. and 42° C. for 2 minutes and 10 minutes, respectively, before the reaction mixture was adjusted to a final concentration of 20 μg/ml reverse transcriptase. After incubation at 42° C. for 1.5 hours the reaction was stopped by addition of sodium hydroxide to 0.2M. After 30 minutes at 65° C. the reaction was neutralized with an equal amount of hydrochloric acid and Tris-HCl was added to a concentration of 0.08M, pH 7.5. The reaction was extracted with an equal volume of chloroform:isoamyl alcohol (24:1, vol./vol.) and the organic phase was extracted twice with 10mM Tris-HCl, pH 7.5, 1mM EDTA. The aqueous phases were pooled and the cDNA was separated from unincorporated label by gel permeation chromatography through a column of Sephadex G-75 as described previously.

An *E. coli* strain, HB101, carrying the pPVL 134 plasmid described herein has been deposited with the American Type Culture Collection, Rockville, Md., and has been assigned accession number ATCC 39181. The invention described and claimed herein is not to be limited in scope by the microorganism deposited, since the deposited embodiment is intended as a single illustration of one aspect of the invention and mutants, recombinants and equivalent microorganisms (or plasmids) which produce functionally equivalent proteins are within the scope of this invention. Indeed, various modifications of the invention in addition to those shown and described herein will become apparent to those skilled in the art from the foregoing description. Such modifications are also intended to fall within the scope of the appended claims.

We claim:

1. A substantially pure DNA sequence coding for lectin protein, consisting essentially of the sequence:

ATG GCT TCC TCC AAG TTA CTC TCC CTA
GCC CTC TTC CTT GCG CTT CTC AGC
CAC GCA AAC TCA GCC ACC GAA ACC
TCC TTC ATC ATC GAT GCG TTC AAC
AAA ACC AAC CTT ATC CTT CAA GGC
GAT GCC ACC GTC TCA TCC AAC GGC
AAC TTA CAA CTA TCC TAT AAT TCA
TAC GAC TCT ATG AGC AGA GCC TTC
TAC TCC GCC CCC ATC CAA ATC AGG
GAC AGC ACC ACC GGC AAC GTC GGC
AGC TTC GAC ACC AAC TTC ACA ATG
AAT ATC CGC ACT CAC CGC CAA GCA
ATT TCC GCC GTT GGC CTT GAC TTT
GTT CTC GTC CCC GTC CAG CCC GAA
TCC AAA GGC GAT ACT GTG ACT GTG
GAG TTC GAC ACC TTC CTC AGC CGT
ATT AGC ATC GAC GTG AAC AAC AAC
GAT ATC AAA AGC GTG CTT TGG GAT
GTA CAC GAC TAC GAC GGA CAA AAC
GCC GAG GTT CGG ATC ACC TAT AAC
TCC TCC ACG AAG GTC TTC TCG GTT
TCT CTG TCA AAC CCT TCT ACG GGA
AAG AGC AAC AAC GTC TCT ACC ACA
GTG GAG CTG GAG AAA GAA GTT TAC
GAC TGG GTG AGC GTT GGG TTC TCT
GCC ACC TCA GGG GCT TAT CAA TGG
AGC TAT GAA ACG CAC GAC GTC CTC
TCT TGG TCT TTT TCT TCC AAG TTC
ATC AAT CTT AAG GAC CAA AAA TCT
GAA CGT TCC AAC ATC GTC CTC AAC
AAG ATC CTC TAG.

2. A substantially pure DNA sequence consisting essentially of DNA coding for a *Phaseolus vulgaris* lectin protein, said protein having the amino acid sequence encoded by the DNA sequence of claim 1.

3. A substantially pure DNA sequence coding for a *Phaseolus vulgaris* lectin protein consisting essentially of a DNA sequence which hybridizes under Southern hybridization conditions with the DNA sequence of claim 1.

4. A recombinant vector, comprising a vector and the DNA sequence of claim 1.

5. A recombinant vector, comprising a vector and the DNA sequence of claim 2.

6. A recombinant vector, comprising a vector and the DNA sequence of claim 3.

7. A recombinant vector, comprising a vector and the DNA sequence of claim 1, which recombinant vector is capable of being replicated, transcribed and translated in a unicellular organism.

8. A recombinant vector, comprising a vector and the DNA sequence of claim 2, which recombinant vector is capable of being replicated, transcribed and translated in a unicellular organism.

9. A recombinant vector, comprising a vector and the DNA sequence of claim 3, which recombinant vector is capable of being replicated, transcribed and translated in a unicellular organism.

10. The recombinant vector of claim 7 in which the DNA sequence is under the control of expression control elements.

11. The recombinant vector of claim 4 in which the DNA sequence is under the control of expression control elements.

12. The recombinant vector of claim 9 in which the DNA sequence is under the control of expression control elements.

13. A unicellular organism containing the vector of claim 4.

14. A unicellular organism containing the vector of claim 6.

15. The recombinant vector of claim 6 in which said vector is in an *Escherichia coli* bacterium.

16. The recombinant vector of claim 15 in which said vector is the recombinant vector in the Escherichia coli bacterium deposited with the ATCC and assigned accession no. 39181, or in a mutant or recombinant thereof.

17. A process for producing a *Phaseolus vulgaris* lectin protein comprising:
 a. culturing a unicellular organism containing the recombinant vector of claim 10 coding for lectin protein and capable of being replicated, transcribed and translated in said unicellular organism; and
 b. isolating lectin protein from the culture.

18. A process for producing a *Phaseolus vulgaris* lectin protein comprising:
 a. culturing a unicellular organism containing the recombinant vector of claim 11 coding for lectin protein and capable of being replicated, transcribed and translated in said unicellular organism; and
 b. isolating lectin protein from the culture.

19. A process for producing a *Phaseolus vulgaris* lectin protein comprising:
 a. culturing a unicellular organism containing the recombinant vector of claim 12 coding for lectin protein and capable of being replicated, transcribed and translated in said unicellular organism; and
 b. isolating lectin protein from the culture.

20. The process according to claim 17 in which the recombinant vector is introduced into the unicellular organism by transformation.

21. The process according to claim 18 in which the recombinant vector is introduced into the unicellular organism by transformation.

22. The process according to claim 19 in which the recombinant vector is introduced into the unicellular organism by transformation.

23. The process according to claim 17 in which the recombinant vector is introduced into the unicellular organism by transfection.

24. The process according to claim 18 in which the recombinant vector is introduced into the unicellular organism by transfection.

25. The process according to claim 19 in which the recombinant vector is introduced into the unicellular organism by transfection.

26. The process according to claim 17 in which the DNA sequence is obtained by isolating mRNA coding for lectin protein and using reverse transcriptase to construct said DNA sequence.

27. The process according to claim 18 in which the DNA sequence is obtained by isolating mRNA coding for lectin protein and using reverse transcriptase to construct said DNA sequence.

28. The process according to claim 19 in which the DNA sequence is obtained by isolating mRNA coding for lectin protein and using reverse transcriptase to construct said DNA sequence.

29. The process according to claim 17 in which the unicellular organism is a eucaryotic organism.

30. The process according to claim 18 in which the unicellular organism is a eucaryotic organism.

31. The process according to claim 19 in which the unicellular organism is a eucaryotic organism.

32. The process according to claim 17 in which the unicellular orgnaism is a procaryotic organism.

33. The process according to claim 18 in which the unicellular organism is a procaryotic organism.

34. The process according to claim 19 in which the unicellular organism is a procaryotic organism.

35. The process according to claim 32 in which the unicellular organism is *Escherichia coli.*

36. The process according to claim 33 in which the unicellular organism is *Escherichia coli.*

37. The process according to claim 34 in which the unicellular organism is *Escherichia coli.*

38. A process for preparing a unicellular organism having a DNA sequence coding for a *Phaseolus vulgaris* lectin protein comprising introducing into a unicellular organism the recombinant vector of claim 10 coding for said lectin protein and capable of being replicated, transcribed and translated in the unicellular organism.

39. A process for preparing a unicellular organism having a DNA sequence coding for a *Phaseolus vulgaris* lectin protein comprising introducing into a unicellular organism the recombinant vector of claim 11 coding for said lectin protein and capable of being replicated, transcribed and translated in the unicellular organism.

40. A process for preparing a unicellular organism having a DNA sequence coding for a *Phaseolus vulgaris* lectin protein comprising introducing into a unicellular organism the recombinant vector of claim 12 coding for said lectin protein and capable of being replicated, transcribed and translated in the unicellular organism.

* * * * *

UNITED STATES PATENT AND TRADEMARK OFFICE
CERTIFICATE OF CORRECTION

Page 1 of 2

PATENT NO. : 4,870,015
DATED : September 26, 1989
INVENTOR(S) : Hoffman, Leslie M.

It is certified that error appears in the above-identified patent and that said Letters Patent is hereby corrected as shown below:

At column 1, line 68, please rewrite "glygcoproteins" as --glycoproteins--. At column 3, line 53, please delete "the". At column 5, line 35, please rewrite "chromatrography" as --chromatography--. At column 6, line 17, please rewrite "litgating" as --ligating--. At column 8, line 21, please rewrite "an dthen" as --and then--. At column 9, line 11, please rewrite "describeed" as --described--. At column 9, line 44, please rewrite "ampicilin" as --ampicillin--. At column 10, line 38, please rewrite "coliphase" as --coliphage--. At column 11, line 17, please rewrite "(DDT," as --(DTT,--. At column 12, line 12, please rewrite "gradients" as --gradient--. At column 13, bridging lines 12 & 13, please rewrite "oligo(-cytidylic acid)" as --oligo(cytidylic acid)--. At column 13, line 25, please rewrite "biascrylamide" as --bisacrylamide--. At column 13, line 33, please rewrite "hour" as --hours--. At column 13, line 47, please rewrite "reciprocated" as --reprecipitated--. At column 13, lines 47-48, please rewrite "ethanol, redissolved" as --ethanol, and redissolved--. At column 14, line 5, please rewrite "bwas" as --was--. At column 14, line 10, please rewrite "absorbence" as --absorbance--. At column 14, line 21, please rewrite "hour" as --hours--. At column 14, line 44, please rewrite "Tris-CH1" as --Tris-HCl--. At column 15, line 37, please rewrite "transciptase" as --transcriptase--. At column 16, claim 1, line 18, please rewrite "GTG CTT TGG" as --GTG CCT TGG--. At column 17, claim 16, line 9, please rewrite "Escherichia coli" as --_Escherichia coli_--.

UNITED STATES PATENT AND TRADEMARK OFFICE
CERTIFICATE OF CORRECTION

PATENT NO. : 4,870,015

DATED : September 26, 1989

INVENTOR(S) : Hoffman, Leslie M.

It is certified that error appears in the above-identified patent and that said Letters Patent is hereby corrected as shown below:

At column 18, claim 32, line 23, please rewrite "orgnaism" as --organism--.

Signed and Sealed this

Twenty-seventh Day of November, 1990

Attest:

HARRY F. MANBECK, JR.

*Attesting Officer*   *Commissioner of Patents and Trademarks*